US00PP28576P2

(12) United States Plant Patent
Pavlich

(10) Patent No.: US PP28,576 P2
(45) Date of Patent: Oct. 24, 2017

(54) ×*HEUCHERELLA* PLANT NAMED 'TNHERHHL'

(50) Latin Name: ×*Heucherella* hybrid
Varietal Denomination: TNHERHHL

(71) Applicant: Terra Nova Nurseries, Inc., Canby, OR (US)

(72) Inventor: John C. Pavlich, Olympia, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 14/999,756

(22) Filed: Jun. 22, 2016

(51) Int. Cl.
*A01H 5/12* (2006.01)

(52) U.S. Cl.
USPC ..... Plt./441

(58) Field of Classification Search
USPC ..... Plt./441
CPC ..... A01H 5/12; A01H 5/02; A01H 5/00
See application file for complete search history.

*Primary Examiner* — June Hwu
(74) *Attorney, Agent, or Firm* — Klarquist Sparkman, LLP

(57) ABSTRACT

A new and distinct ×*Heucherella* plant substantially as shown and described, characterized by solid lime green colored leaves for most of the year, distinctively lobed, palmately divided leaves, small white flowers on short flower stalks, a medium plant size with multiple crowns, and excellent vigor.

1 Drawing Sheet

Botanical denomination: ×*Heucherella* hybrid.
Variety designation: 'TNHERHHL'.
Cross reference to ×*Heucherella* 'Buttered Rum' (U.S. Plant Pat. No. 25,040) and ×*Heucherella* 'Mojito' (U.S. Plant Pat. No. 26,946).

BACKGROUND OF THE INVENTION

The present invention relates to a new and distinct cultivar of ×*Heucherella* and given the cultivar name of 'TNHERHHL'. ×*Heucherella* is in the family Saxifragaceae. ×*Heucherella* 'TNHERHHL' originated from a whole plant mutation of ×*Heucherella* 'Buttered Rum' (U.S. Plant Pat. No. 25,040), found in the greenhouse in Canby, Oreg.

Compared to ×*Heucherella* 'Buttered Rum' (U.S. Plant Pat. No. 25,040), this new cultivar has solid lime leaves rather than orange amber to red brown leaves with a red pattern on the veins.

Compared to ×*Heucherella* 'Mojito' (U.S. Plant Pat. No. 26,946), the new cultivar is solid lime green rather than yellow to yellow green with a red center.

SUMMARY OF THE INVENTION

The following traits have been repeatedly observed and are determined to be the unique characteristics of 'TNHERHHL'. This new ×*Heucherella* is unique in having the following characteristics:

1. solid lime green colored leaves for most of the year,
2. distinctively lobed, palmately divided leaves,
3. small white flowers on short flower stalks
4. medium plant size with multiple crowns, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a four-month-old ×*Heucherella* 'TNHERHHL' growing in a 4" pot in a cool greenhouse in February in Canby, Oreg.

FIG. 2 shows a nine-month-old in flower growing in a one gallon container in the greenhouse in early spring in Canby, Oreg.

FIG. 3 shows a one-year-old ×*Heucherella* 'TNHERHHL' in a one gallon container in the greenhouse trial bed in February in Canby, Oreg.

DETAILED PLANT DESCRIPTION

The following is a detailed description of the new ×*Heucherella* cultivar based on observations of one-year-old specimens growing in one gallon containers in a cool greenhouse in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart*, fifth edition, 2007.

Plant:

*Form*.—Basal rosette, herbaceous perennial.
*Hardiness*.—USDA Zone 4 to 9.
*Size*.—20 cm tall from top of the foliage to the ground and 42 cm wide.
*Habit*.—Mounding.
*Vigor*.—Excellent.

*Roots*.—Fibrous, freely branching, fine, and white in color. Roots develop easily from cuttings.

Leaf:

*Type*.—Simple.

*Arrangement*.—Rosette.

*Shape*.—Broadly ovate.

*Lobing/division*.—5 palmate lobes, the terminal lobe the most prominent.

*Venation*.—palmate, topside Yellow Green 145A on young leaves, Greyed Red 183A on old leaves in cold temperatures, bottom side Yellow Green 145B on young leaves, Greyed Red 183A on old leaves in cold temperatures.

*Margins*.—Broadly crenate.

*Apex*.—Mucronulate.

*Base*.—Cordate.

*Blade size*.—Grows to 10 cm long and 10.5 cm wide.

*Surface texture*.—Glandular pubescent on both surfaces.

*Petiole description*.—Grows to 20 cm long and 2 mm wide, glandular hairs, Yellow Green N144A with base tinted Greyed 183A; older leaves Greyed Red 183A.

*Leaf color*.—Spring, summer, and fall topside, Yellow Green 145A, bottom side Yellow Green 145B; winter Yellow Green 145A sometimes with veins Greyed Red 183A or tinted Greyed Orange 165A overall, older leaves margins turn Greyed Red 179D.

Inflorescence:

*Size*.—Grows to 2.4 cm wide and 8 cm long.

*Type*.—Raceme.

*Attitude*.—Upright.

*Number of flowers per raceme*.—About 45.

*Number of raceme*.—30.

*Peduncle*.—Grows to 21 cm tall, 2.5 mm wide at base, Yellow Green N144A with Greyed Red 183A, glandular hairs.

*Pedicel*.—2.5 mm long, with glandular hairs, Yellow Green N144A.

*Bloom period*.—April in Canby, Oreg.

Flower bud:

*Size*.—2 mm wide and 3 mm long.

*Description*.—Glandular puberulent, ovoid.

*Color*.—White NN155C.

Flower:

*Type*.—Imperfect.

*Shape*.—Campanulate.

*Size*.—4 mm deep and 5 mm wide.

*Attitude*.—Side-facing.

*Petal description*.—5 in number, linear, 3.5 mm long and less than 1 mm wide, tip acuminate, base attenuate, margin entire, glabrous on both sides, White NN155D on both sides.

*Calyx description*.—4 mm deep and 5 mm wide, with 5 lobes, divided ¾ way to the base, campanulate, glandular hairs on outside, glabrous inside, tip obtuse, margin entire, NN155D on both sides.

*Stamen description*.—10, filaments 2 mm long White NN155D, anthers Greyed Orange 164A, pollen none, sterile.

*Pistil description*.—One central two beaked pistil, 4.5 mm long and 2 mm wide, White NN155D.

*Fragrance*.—None.

*Lastingness*.—Each raceme blooms for about 2 weeks on the plant.

Fruit and seed: None.

Disease and pest tolerance: The new cultivar is typical to the genus. No known resistances to pests or diseases. No problems have been found in Canby, Oreg.

I claim:

1. A new and distinct ×*Heucherella* plant as herein illustrated and described.

* * * * *

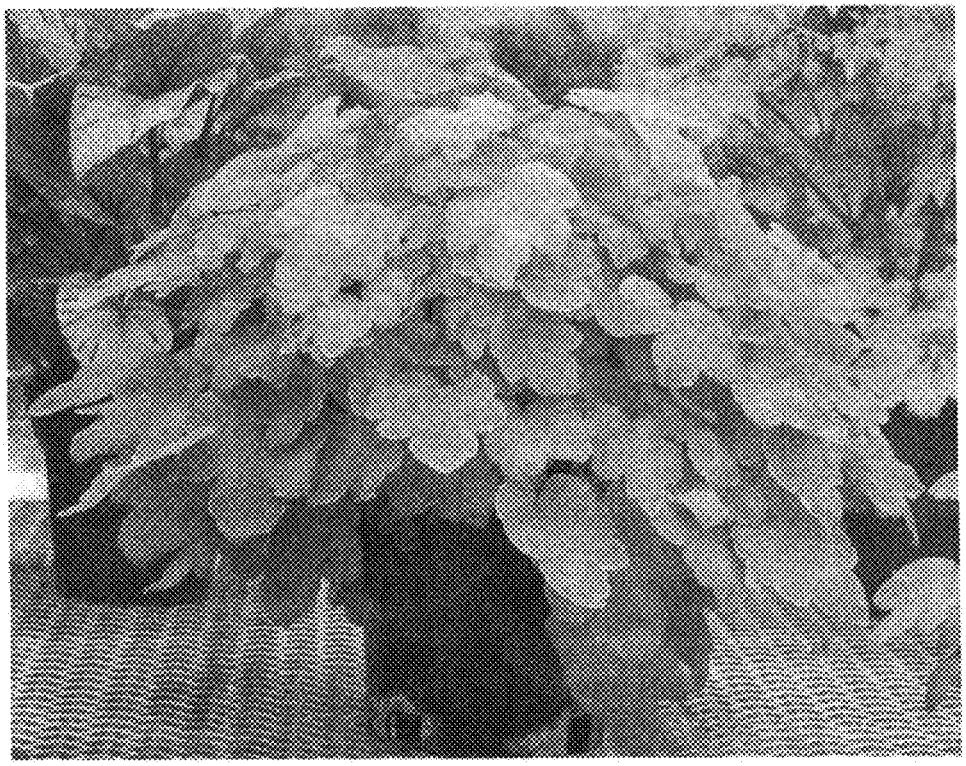

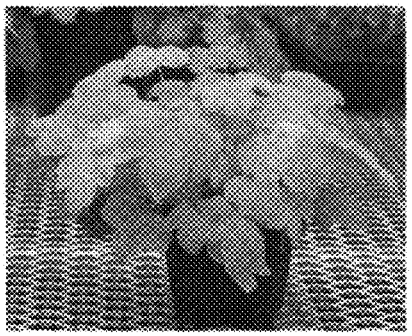
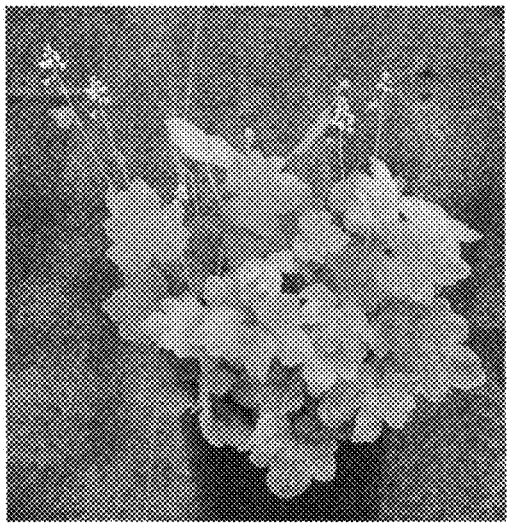
FIG. 1 above, FIG. 2 on right,
FIG. 3 below